US008434208B2

(12) United States Patent
Jacobsen et al.

(10) Patent No.: US 8,434,208 B2
(45) Date of Patent: May 7, 2013

(54) TWO-DIMENSIONAL LAYOUT FOR USE IN A COMPLEX STRUCTURE

(75) Inventors: Stephen C. Jacobsen, Salt Lake City, UT (US); David P. Marceau, Salt Lake City, UT (US)

(73) Assignee: Raytheon Company, Waltham, MA (US)

( * ) Notice: Subject to any disclaimer, the term of this patent is extended or adjusted under 35 U.S.C. 154(b) by 0 days.

(21) Appl. No.: 13/181,380

(22) Filed: Jul. 12, 2011

(65) Prior Publication Data

US 2011/0268914 A1 Nov. 3, 2011

Related U.S. Application Data

(62) Division of application No. 12/151,730, filed on May 7, 2008, now Pat. No. 8,002,716.

(60) Provisional application No. 60/928,149, filed on May 7, 2007.

(51) Int. Cl.
*B28B 5/00* (2006.01)
*B29C 63/00* (2006.01)
*B29C 65/00* (2006.01)
*B29C 69/00* (2006.01)
*B21D 39/03* (2006.01)
*B23P 11/00* (2006.01)

(52) U.S. Cl.
USPC ............................................ 29/428; 264/241

(58) Field of Classification Search .................. 600/585; 264/241; 29/592, 428–431
See application file for complete search history.

(56) References Cited

U.S. PATENT DOCUMENTS 1,107,874 A 8/1914 Appleby
1,112,460 A 10/1914 Leavitt
(Continued)

FOREIGN PATENT DOCUMENTS

CA 2512299 9/2004
CN 1603068 4/2005
(Continued)

OTHER PUBLICATIONS

U.S. Appl. No. 12/814,302, filed Jun. 11, 2010; Stephen C. Jacobsen; office action issued Jan. 10, 2012.
(Continued)

*Primary Examiner* — Max Hindenburg
*Assistant Examiner* — John Pani
(74) *Attorney, Agent, or Firm* — Thorpe North & Western LLP

(57) ABSTRACT

A method for manufacturing a complex structure from a two-dimensional layout, the method comprising: (a) obtaining a support plate having a pre-determined, patterned recess formed in a surface thereof; (b) depositing a first series of individual flexible interconnects into the recess, the flexible interconnects being aligned parallel to one another in a common plane and supported by the support plate; (c) adhering, with adhering means, at least one rigid member to each of the flexible interconnects of the first series; (d) adhering, with adhering means, a second series of individual flexible interconnects to the rigid members to form a plurality of stations, wherein each of the second series of flexible interconnects is adhered to two rigid members of adjacent flexible interconnects of the first series, the flexible interconnects of the second series being formed perpendicular to the flexible interconnects of the first series; (e) curing the adhering means to form an assembled, layered structure; (f) removing the layered structure from the support plate; and (g) folding, systematically, the layered structure on itself and causing at least some of the stations to be supported about a central spine in a segmented manner.

11 Claims, 7 Drawing Sheets

U.S. PATENT DOCUMENTS

| | | |
|---|---|---|
| 1,515,756 A | 11/1924 | Roy |
| 1,975,726 A | 10/1934 | Martinage |
| 2,025,999 A | 12/1935 | Myers |
| 2,082,920 A | 6/1937 | Aulmont |
| 2,129,557 A | 9/1938 | Beach |
| 2,312,072 A | 3/1940 | Broadwater |
| 2,311,475 A | 2/1943 | Schmeiser |
| 2,329,582 A | 9/1943 | Bishop |
| 2,345,763 A | 4/1944 | Mayne |
| 2,701,169 A | 2/1955 | Cannon |
| 2,850,147 A | 9/1958 | Hill |
| 2,933,143 A | 4/1960 | Robinson |
| 2,967,737 A | 1/1961 | Moore |
| 3,037,571 A | 6/1962 | Zelle |
| 3,060,972 A | 10/1962 | Sheldon |
| 3,107,643 A | 10/1963 | Edwards |
| 3,166,138 A | 1/1965 | Dunn, Jr. |
| 3,190,286 A | 6/1965 | Stokes |
| 3,215,219 A | 11/1965 | Forsyth |
| 3,223,462 A | 12/1965 | Dalrymple |
| 3,266,059 A | 8/1966 | Stelle |
| 3,284,964 A | 11/1966 | Saito |
| 3,311,424 A | 3/1967 | Taylor |
| 3,362,492 A | 1/1968 | Hansen |
| 3,387,896 A | 6/1968 | Sobota |
| 3,489,236 A | 1/1970 | Goodwin |
| 3,497,083 A | 2/1970 | Anderson |
| 3,565,198 A | 2/1971 | Ames |
| 3,572,325 A | 3/1971 | Bazell |
| 3,609,804 A | 10/1971 | Morrison |
| 3,650,343 A | 3/1972 | Helsell |
| 3,700,115 A | 10/1972 | Johnson |
| 3,707,218 A | 12/1972 | Payne |
| 3,712,481 A | 1/1973 | Harwood |
| 3,715,146 A | 2/1973 | Robertson |
| 3,757,635 A | 9/1973 | Hickerson |
| 3,808,078 A | 4/1974 | Snellman |
| 3,820,616 A | 6/1974 | Juergens |
| 3,841,424 A | 10/1974 | Purcell |
| 3,864,983 A | 2/1975 | Jacobsen |
| 3,933,214 A | 1/1976 | Guibord |
| 3,934,664 A | 1/1976 | Pohjola |
| 3,974,907 A | 8/1976 | Shaw |
| 4,015,553 A | 4/1977 | Middleton |
| 4,051,914 A | 10/1977 | Pohjola |
| 4,059,315 A | 11/1977 | Jolliffe |
| 4,068,905 A | 1/1978 | Black |
| 4,107,948 A | 8/1978 | Maolaug |
| 4,109,971 A | 8/1978 | Black |
| 4,132,279 A | 1/1979 | Van der Lende |
| 4,218,101 A | 8/1980 | Thompson |
| 4,260,053 A | 4/1981 | Onodera |
| 4,332,317 A | 6/1982 | Bahre |
| 4,332,424 A | 6/1982 | Thompson |
| 4,339,031 A | 7/1982 | Densmore |
| 4,393,728 A | 7/1983 | Larson |
| 4,396,233 A | 8/1983 | Slaght |
| 4,453,611 A | 6/1984 | Stacy, Jr. |
| 4,483,407 A | 11/1984 | Iwamoto et al. |
| 4,489,826 A | 12/1984 | Dubson |
| 4,494,417 A | 1/1985 | Larson |
| 4,551,061 A | 11/1985 | Olenick |
| 4,589,460 A | 5/1986 | Albee |
| 4,621,965 A | 11/1986 | Wilcock |
| 4,636,137 A | 1/1987 | Lemelson |
| 4,646,906 A | 3/1987 | Wilcox, Jr. |
| 4,661,039 A | 4/1987 | Brenhold |
| 4,671,774 A | 6/1987 | Owsen |
| 4,700,693 A | 10/1987 | Lia |
| 4,706,506 A | 11/1987 | Lestelle |
| 4,712,969 A | 12/1987 | Kimura |
| 4,713,896 A | 12/1987 | Jennens |
| 4,714,125 A | 12/1987 | Stacy, Jr. |
| 4,727,949 A | 3/1988 | Rea |
| 4,736,826 A | 4/1988 | White et al. |
| 4,752,105 A | 6/1988 | Barnard |
| 4,756,662 A | 7/1988 | Tanie |
| 4,765,795 A | 8/1988 | Rebman |
| 4,784,042 A | 11/1988 | Paynter |
| 4,796,607 A | 1/1989 | Allred, III |
| 4,806,066 A | 2/1989 | Rhodes |
| 4,815,319 A | 3/1989 | Clement |
| 4,815,911 A | 3/1989 | Bengtsson |
| 4,818,175 A | 4/1989 | Kimura |
| 4,828,339 A | 5/1989 | Thomas |
| 4,848,179 A | 7/1989 | Ubhayakar |
| 4,862,808 A | 9/1989 | Hedgecoxe |
| 4,878,451 A | 11/1989 | Siren |
| 4,900,218 A | 2/1990 | Sutherland |
| 4,909,341 A | 3/1990 | Rippingale |
| 4,924,153 A | 5/1990 | Toru et al. |
| 4,932,491 A | 6/1990 | Collins, Jr. |
| 4,932,831 A | 6/1990 | White et al. |
| 4,936,639 A | 6/1990 | Pohjola |
| 4,997,790 A | 3/1991 | Woo |
| 5,018,591 A | 5/1991 | Price |
| 5,021,798 A | 6/1991 | Ubhayakar |
| 5,022,812 A | 6/1991 | Coughlan |
| 5,046,914 A | 9/1991 | Holland et al. |
| 5,080,000 A | 1/1992 | Bubic |
| 5,130,631 A | 7/1992 | Gordon |
| 5,142,932 A | 9/1992 | Moya |
| 5,174,168 A | 12/1992 | Takagi |
| 5,174,405 A | 12/1992 | Carra |
| 5,186,526 A | 2/1993 | Pennington |
| 5,199,771 A | 4/1993 | James |
| 5,205,612 A | 4/1993 | Sugden et al. |
| 5,214,858 A | 6/1993 | Pepper |
| 5,219,264 A | 6/1993 | McClure et al. |
| 5,252,870 A | 10/1993 | Jacobsen |
| 5,297,443 A | 3/1994 | Wentz |
| 5,317,952 A | 6/1994 | Immega |
| 5,337,732 A | 8/1994 | Grundfest |
| 5,337,846 A | 8/1994 | Ogaki et al. |
| 5,350,033 A | 9/1994 | Kraft |
| 5,354,124 A | 10/1994 | James |
| 5,363,935 A | 11/1994 | Schempf |
| 5,386,741 A | 2/1995 | Rennex |
| 5,413,454 A | 5/1995 | Movsesian |
| 5,426,336 A | 6/1995 | Jacobsen |
| 5,428,713 A | 6/1995 | Matsumaru |
| 5,435,405 A | 7/1995 | Schempf |
| 5,440,916 A | 8/1995 | Stone et al. |
| 5,443,354 A | 8/1995 | Stone et al. |
| 5,451,135 A | 9/1995 | Schempf |
| 5,465,525 A | 11/1995 | Mifune |
| 5,466,056 A | 11/1995 | James |
| 5,469,756 A | 11/1995 | Feiten |
| 5,516,249 A | 5/1996 | Brimhall |
| 5,519,814 A | 5/1996 | Rodriguez et al. |
| 5,551,545 A | 9/1996 | Gelfman |
| 5,556,370 A | 9/1996 | Maynard |
| 5,562,843 A | 10/1996 | Yasumoto |
| 5,567,110 A | 10/1996 | Sutherland |
| 5,570,992 A | 11/1996 | Lemelson |
| 5,573,316 A | 11/1996 | Wankowski |
| 5,588,688 A | 12/1996 | Jacobsen |
| 5,672,044 A | 9/1997 | Lemelson |
| 5,697,285 A | 12/1997 | Nappi |
| 5,712,961 A | 1/1998 | Matsuo |
| 5,749,828 A | 5/1998 | Solomon |
| 5,770,913 A | 6/1998 | Mizzi |
| 5,816,769 A | 10/1998 | Bauer |
| 5,821,666 A | 10/1998 | Matsumoto |
| 5,842,381 A | 12/1998 | Feiten |
| RE36,025 E | 1/1999 | Suzuki |
| 5,878,783 A | 3/1999 | Smart |
| 5,888,235 A | 3/1999 | Jacobsen |
| 5,902,254 A | 5/1999 | Magram |
| 5,906,591 A | 5/1999 | Dario |
| 5,984,032 A | 11/1999 | Gremillion |
| 5,996,346 A | 12/1999 | Maynard |
| 6,016,385 A | 1/2000 | Yee |
| 6,030,057 A | 2/2000 | Fikse |
| 6,056,237 A | 5/2000 | Woodland |
| 6,107,795 A | 8/2000 | Smart |
| 6,109,705 A | 8/2000 | Courtemanche |

| | | | | | | |
|---|---|---|---|---|---|---|
| 6,113,343 | A | 9/2000 | Goldenberg et al. | 7,415,321 B2 | 8/2008 | Okazaki et al. |
| 6,132,133 | A | 10/2000 | Muro et al. | 7,475,745 B1 | 1/2009 | DeRoos |
| 6,138,604 | A | 10/2000 | Anderson | 7,539,557 B2 | 5/2009 | Yamauchi |
| 6,162,171 | A | 12/2000 | Ng | 7,546,912 B1 | 6/2009 | Pack et al. |
| 6,186,604 | B1 | 2/2001 | Fikse | 7,597,162 B2 | 10/2009 | Won |
| 6,203,126 | B1 | 3/2001 | Harguth | 7,600,592 B2 | 10/2009 | Goldenberg et al. |
| 6,260,501 | B1 | 7/2001 | Agnew | 7,645,110 B2 | 1/2010 | Ogawa et al. |
| 6,263,989 | B1 | 7/2001 | Won | 7,654,348 B2 | 2/2010 | Ohm et al. |
| 6,264,293 | B1 | 7/2001 | Musselman | 7,775,312 B2 | 8/2010 | Maggio |
| 6,264,294 | B1 | 7/2001 | Musselman et al. | 7,798,264 B2 | 9/2010 | Hutcheson et al. |
| 6,281,489 | B1 | 8/2001 | Tubel et al. | 7,843,431 B2 | 11/2010 | Robbins et al. |
| 6,323,615 | B1 | 11/2001 | Khairallah | 7,845,440 B2 | 12/2010 | Jacobsen |
| 6,325,749 | B1 | 12/2001 | Inokuchi et al. | 7,860,614 B1 | 12/2010 | Reger |
| 6,333,631 | B1 | 12/2001 | Das et al. | 7,974,736 B2 | 7/2011 | Morin et al. |
| 6,339,993 | B1 | 1/2002 | Comello | 8,002,716 B2 * | 8/2011 | Jacobsen et al. ............. 600/585 |
| 6,380,889 | B1 | 4/2002 | Herrmann et al. | 8,042,630 B2 | 10/2011 | Jacobsen |
| 6,394,204 | B1 | 5/2002 | Haringer | 8,162,410 B2 | 4/2012 | Hirose et al. |
| 6,405,798 | B1 | 6/2002 | Barrett et al. | 8,205,695 B2 | 6/2012 | Jacobsen et al. |
| 6,408,224 | B1 | 6/2002 | Okamoto | 2001/0037163 A1 | 11/2001 | Allard |
| 6,411,055 | B1 | 6/2002 | Fujita | 2002/0038168 A1 | 3/2002 | Kasuga et al. |
| 6,422,509 | B1 | 7/2002 | Yim | 2002/0128714 A1 | 9/2002 | Manasas et al. |
| 6,430,475 | B2 | 8/2002 | Okamoto | 2002/0140392 A1 | 10/2002 | Borenstein |
| 6,431,296 | B1 | 8/2002 | Won | 2002/0189871 A1 | 12/2002 | Won |
| 6,446,718 | B1 | 9/2002 | Barrett et al. | 2003/0000747 A1 | 1/2003 | Sugiyama |
| 6,450,104 | B1 | 9/2002 | Grant | 2003/0069474 A1 | 4/2003 | Couvillon, Jr. |
| 6,477,444 | B1 | 11/2002 | Bennett et al. | 2003/0097080 A1 * | 5/2003 | Esashi et al. .................. 600/585 |
| 6,484,083 | B1 | 11/2002 | Hayward | 2003/0110938 A1 | 6/2003 | Seto |
| 6,488,306 | B1 | 12/2002 | Shirey et al. | 2003/0223844 A1 | 12/2003 | Schiele |
| 6,505,896 | B1 | 1/2003 | Boivin | 2004/0030571 A1 | 2/2004 | Solomon |
| 6,512,345 | B2 | 1/2003 | Borenstein | 2004/0099175 A1 | 5/2004 | Perrot et al. |
| 6,522,950 | B1 | 2/2003 | Conca et al. | 2004/0103740 A1 | 6/2004 | Townsend |
| 6,523,629 | B1 | 2/2003 | Buttz | 2004/0168837 A1 | 9/2004 | Michaud |
| 6,529,806 | B1 | 3/2003 | Licht | 2004/0216931 A1 | 11/2004 | Won |
| 6,535,793 | B2 | 3/2003 | Allard | 2004/0216932 A1 | 11/2004 | Giovanetti |
| 6,540,310 | B1 | 4/2003 | Cartwright | 2005/0007055 A1 | 1/2005 | Borenstein |
| 6,557,954 | B1 | 5/2003 | Hattori | 2005/0027412 A1 | 2/2005 | Hobson |
| 6,563,084 | B1 | 5/2003 | Bandy | 2005/0085693 A1 | 4/2005 | Belson et al. |
| 6,574,958 | B1 | 6/2003 | Macgregor | 2005/0107669 A1 | 5/2005 | Couvillon, Jr. |
| 6,576,406 | B1 | 6/2003 | Jacobsen et al. | 2005/0115337 A1 | 6/2005 | Tarumi |
| 6,595,812 | B1 | 7/2003 | Haney | 2005/0166413 A1 | 8/2005 | Crampton |
| 6,610,007 | B2 | 8/2003 | Belson | 2005/0168068 A1 | 8/2005 | Courtemanche et al. |
| 6,619,146 | B2 | 9/2003 | Kerrebrock | 2005/0168070 A1 | 8/2005 | Dandurand |
| 6,636,781 | B1 | 10/2003 | Shen et al. | 2005/0225162 A1 | 10/2005 | Gibbins |
| 6,651,804 | B2 | 11/2003 | Thomas | 2005/0235898 A1 | 10/2005 | Hobson |
| 6,652,164 | B2 | 11/2003 | Stiepel et al. | 2005/0235899 A1 | 10/2005 | Yamamoto |
| 6,668,951 | B2 | 12/2003 | Won | 2005/0288819 A1 | 12/2005 | de Guzman |
| 6,708,068 | B1 | 3/2004 | Sakaue | 2006/0000137 A1 | 1/2006 | Valdivia y Alvarado |
| 6,715,575 | B2 | 4/2004 | Karpik | 2006/0005733 A1 | 1/2006 | Rastegar et al. |
| 6,725,128 | B2 | 4/2004 | Hogg et al. | 2006/0010702 A1 | 1/2006 | Roth |
| 6,772,673 | B2 | 8/2004 | Seto | 2006/0070775 A1 | 4/2006 | Anhalt |
| 6,773,327 | B1 | 8/2004 | Felice | 2006/0117324 A1 | 6/2006 | Alsafadi et al. |
| 6,774,597 | B1 | 8/2004 | Borenstein | 2006/0156851 A1 | 7/2006 | Jacobsen |
| 6,799,815 | B2 | 10/2004 | Krishnan | 2006/0225928 A1 | 10/2006 | Nelson |
| 6,820,653 | B1 | 11/2004 | Schempf | 2006/0229773 A1 | 10/2006 | Peretz |
| 6,831,436 | B2 | 12/2004 | Gonzalez | 2006/0290779 A1 | 12/2006 | Reverte et al. |
| 6,835,173 | B2 | 12/2004 | Couvillon, Jr. | 2007/0029117 A1 | 2/2007 | Goldenberg et al. |
| 6,837,318 | B1 | 1/2005 | Craig | 2007/0156286 A1 | 7/2007 | Yamauchi |
| 6,840,588 | B2 | 1/2005 | Deland | 2007/0193790 A1 | 8/2007 | Goldenberg et al. |
| 6,866,671 | B2 | 3/2005 | Tierney | 2007/0260378 A1 | 11/2007 | Clodfelter |
| 6,870,343 | B2 | 3/2005 | Borenstein | 2007/0293989 A1 | 12/2007 | Norris |
| 6,889,118 | B2 | 5/2005 | Murray et al. | 2008/0115687 A1 | 5/2008 | Gal et al. |
| 6,917,176 | B2 | 7/2005 | Schempf | 2008/0164079 A1 | 7/2008 | Jacobsen |
| 6,923,693 | B2 | 8/2005 | Borgen | 2008/0167752 A1 | 7/2008 | Jacobsen |
| 6,936,003 | B2 | 8/2005 | Iddan | 2008/0168070 A1 | 7/2008 | Naphade |
| 6,959,231 | B2 | 10/2005 | Maeda | 2008/0215185 A1 | 9/2008 | Jacobsen |
| 7,020,701 | B1 | 3/2006 | Gelvin et al. | 2008/0272647 A9 | 11/2008 | Hirose et al. |
| 7,040,426 | B1 | 5/2006 | Berg | 2008/0284244 A1 | 11/2008 | Hirose et al. |
| 7,044,245 | B2 | 5/2006 | Anhalt et al. | 2009/0035097 A1 | 2/2009 | Loane |
| 7,069,124 | B1 | 6/2006 | Whittaker et al. | 2009/0171151 A1 | 7/2009 | Choset et al. |
| 7,090,637 | B2 | 8/2006 | Danitz | 2009/0212157 A1 | 8/2009 | Arlton et al. |
| 7,137,465 | B1 | 11/2006 | Kerrebrock | 2010/0030377 A1 | 2/2010 | Unsworth |
| 7,144,057 | B1 | 12/2006 | Young et al. | 2010/0036544 A1 | 2/2010 | Mashiach |
| 7,171,279 | B2 | 1/2007 | Buckingham et al. | 2010/0201185 A1 | 8/2010 | Jacobsen et al. |
| 7,188,473 | B1 | 3/2007 | Asada | 2010/0201187 A1 | 8/2010 | Jacobsen |
| 7,188,568 | B2 | 3/2007 | Stout | 2010/0258365 A1 | 10/2010 | Jacobsen |
| 7,228,203 | B2 | 6/2007 | Koselka et al. | 2010/0268470 A1 | 10/2010 | Kamal et al. |
| 7,235,046 | B2 | 6/2007 | Anhalt et al. | 2010/0317244 A1 | 12/2010 | Jacobsen et al. |
| 7,331,436 | B1 | 2/2008 | Pack et al. | 2010/0318242 A1 | 12/2010 | Jacobsen |
| 7,387,179 | B2 | 6/2008 | Anhalt et al. | 2012/0205168 A1 | 8/2012 | Flynn et al. |

FOREIGN PATENT DOCUMENTS

| | | |
|---|---|---|
| CN | 2774717 | 4/2006 |
| CN | 1970373 | 5/2007 |
| DE | 3025840 | 2/1982 |
| DE | 3626238 | 2/1988 |
| DE | 19617852 | 10/1997 |
| DE | 19714464 | 10/1997 |
| DE | 19704080 | 8/1998 |
| DE | 10018075 | 1/2001 |
| DE | 102004010089 | 9/2005 |
| EP | 0105418 | 4/1984 |
| EP | 0584520 | 3/1994 |
| EP | 0818283 | 1/1998 |
| EP | 0924034 | 6/1999 |
| EP | 1444043 | 8/2004 |
| EP | 1510896 | 3/2005 |
| EP | 1832501 | 9/2007 |
| EP | 1832502 | 9/2007 |
| FR | 2638813 | 5/1990 |
| FR | 2660730 | 10/1991 |
| FR | 2850350 | 7/2004 |
| GB | 1199729 | 7/1970 |
| JP | 52 57625 | 5/1977 |
| JP | 52122431 | 9/1977 |
| JP | 58-89480 | 5/1983 |
| JP | SHO 58-80387 | 5/1983 |
| JP | 59139494 | 9/1984 |
| JP | 60015275 | 1/1985 |
| JP | 60047771 | 3/1985 |
| JP | 60060516 | 4/1985 |
| JP | 60139576 | 7/1985 |
| JP | 61001581 | 1/1986 |
| JP | SHO 61-1581 | 1/1986 |
| JP | SHO61-020484 | 2/1986 |
| JP | SHO61-054378 | 3/1986 |
| JP | SHO61-075069 | 4/1986 |
| JP | 61089182 | 5/1986 |
| JP | SHO 63-32084 | 3/1988 |
| JP | 63306988 | 12/1988 |
| JP | 04092784 | 3/1992 |
| JP | HEI 5-3087 | 1/1993 |
| JP | 05147560 | 6/1993 |
| JP | HEI05-270454 | 10/1993 |
| JP | HEI 5-286460 | 11/1993 |
| JP | 06-115465 | 4/1994 |
| JP | HEI 8-133141 | 11/1994 |
| JP | 2007-216936 | 8/1995 |
| JP | 7329841 | 12/1995 |
| JP | HEI 7-329837 | 12/1995 |
| JP | HEI 9-142347 | 6/1997 |
| JP | HEI 11-347970 | 12/1999 |
| JP | 2003-237618 | 2/2002 |
| JP | 2003-019985 | 1/2003 |
| JP | 2003-315486 | 11/2003 |
| JP | 03535508 | 6/2004 |
| JP | 2005-081447 | 3/2005 |
| JP | 2005111595 | 4/2005 |
| JP | 2007-237991 | 9/2007 |
| JP | 2010-509129 | 3/2010 |
| WO | WO 87/02635 | 5/1987 |
| WO | WO97/26039 | 7/1997 |
| WO | WO 00/10073 | 2/2000 |
| WO | WO00/10073 | 2/2000 |
| WO | WO02/16995 | 2/2002 |
| WO | WO03/030727 | 4/2003 |
| WO | WO03037515 | 5/2003 |
| WO | WO 2004/056537 | 7/2004 |
| WO | WO2005/018428 | 3/2005 |
| WO | WO2006068080 | 6/2006 |
| WO | WO 2008/049050 | 4/2008 |
| WO | WO2008/076194 | 6/2008 |
| WO | WO 2008/135978 | 11/2008 |
| WO | WO2009/009673 | 1/2009 |

OTHER PUBLICATIONS

U.S. Appl. No. 11/985,336, filed Nov. 13, 2007; Stephen C. Jacobsen; Notice of Allowance issued Jan. 19, 2012.

U.S. Appl. No. 12/171,146, filed Jul. 10, 2008; Stephen C. Jacobsen; office action issued Feb. 9, 2012.

U.S. Appl. No. 12/765,618, filed Apr. 22, 2010; Stephen C. Jacobsen; notice of allowance issued Feb. 2, 2012.

Mehling et al.; A Minimally Invasive Tendril Robot for In-Space Inspection, Feb. 2006; The First IEEE/RAS-EMBS International Conference on Biomedical Robotics and Biomechatronics (BioRob '06); pp. 690-695.

U.S. Appl. No. 12/350,693, filed Jan. 8, 2009; Stephen C. Jacobsen; office action issued Mar. 28, 2012.

U.S. Appl. No. 12/814,302, filed Jun. 11, 2010; Stephen C. Jacobsen; office action issued Apr. 18, 2012.

U.S. Appl. No. 11/985,320, filed Apr. 25, 2012; Stephen C. Jacobsen; office action issued Apr. 25, 2012.

Arnold, Henry, "Cricket the robot documentation." online manual available at http://www.parallaxinc.com, 22 pages.

Iagnemma, Karl et al., "Traction control of wheeled robotic vehicles in rough terrain with application to planetary rovers." International Journal of Robotics Research, Oct.-Nov. 2004, pp. 1029-1040, vol. 23, No. 10-11.

Hirose, et al., "Snakes and strings; new robotic components for rescue operations," International Journal of Robotics Research, Apr.-May 2004, pp. 341-349, vol. 23, No. 4-5.

Paap et al., "A robot snake to inspect broken buildings," IEEE, 2000, pp. 2079-2082, Japan.

Braure, Jerome, "Participation to the construction of a salamander robot: exploration of the morphological configuration and the locomotion controller", Biologically Inspired Robotics Group, master thesis, Feb. 17, 2004, pp. 1-46.

Jacobsen, et al., Advanced intelligent mechanical sensors (AIMS), Proc. IEEE Trandsucers 1991, Jun. 24-27, abstract only, San Fransico, CA.

Jacobsen, et al., "Research robots for applications in artificial intelligence, teleoperation and entertainment", International Journal of Robotics Research, 2004, pp. 319-330, vol. 23.

Jacobsen, et al., "Multiregime MEMS sensor networks for smart structures," Procs. SPIE 6th Annual Inter. Conf. on Smart Structues and Materials, Mar. 1-5, 1999, pp. 19-32, vol. 3673, Newport Beach CA.

MacLean et al., "A digital MEMS-based strain gage for structural health monitoring," Procs. 1997 MRS Fall Meeting Symposium, Nov. 30-Dec. 4, 1997, pp. 309-320, Boston Massachusetts.

Berlin et al., "MEMS-based control of structural dynamic instability", Journal of Intelligent Material Systems and Structures, Jul. 1998 pp. 574-586, vol. 9.

Goldfarb, "Design and energetic characterization of a liquid-propellant-powered actuator for self-powered robots," IEEE Transactions on Mechatronics, Jun. 2003, vol. 8 No. 2.

Dowling, "Limbless Locomotion: Learning to crawl with a snake robot," The Robotics Institute at Carnegie Mellon University, Dec. 1997, pp. 1-150.

Matthew Heverly & Jaret Matthews: "A wheel-on-limb rover for lunar operation" Internet article, Nov. 5, 2008, pp. 1-8, http://robotics.estec.esa.int/i-SAIRAS/isairas2008/Proceedings/SESSION%2026/m116-Heverly.pdf.

NASA: "Nasa's newest concept vehicles take off-roading out of this world" Internet article, Nov. 5, 2008, http://www.nasa.gov/mission_pages/constellation/main/lunar_truck.html.

Revue Internationale De defense, "3-D vision and urchin" Oct. 1, 1988, p. 1292, vol. 21, No. 10, Geneve CH.

Advertisement, International Defense review, Jane's information group, Nov. 1, 1990, p. 54, vol. 23, No. 11, Great Britain.

Ren Luo "Development of a multibehavior-based mobile robot for remote supervisory control through the internet" IEEE/ ASME Transactions on mechatronics, IEEE Service Center, Piscataway, NY, Dec. 1, 2000, vol. 5, No. 4.

Nilas Sueset et al., "A PDA-based high-level human-robot interaction" Robotics, Automation and Mechatronics, IEEE Conference Singapore, Dec. 1-3, 2004, vol. 2, pp. 1158-1163.

U.S. Appl. No. 11/985,320, filed Nov. 13, 2007; Stephen C. Jacobsen; Office Action issued Aug. 17, 2011.

U.S. Appl. No. 12/171,146, filed Jul. 10, 2008; Stephen C. Jacobsen; office action dated Aug. 20, 2012.

U.S. Appl. No. 12/814,302, filed Jun. 11, 2010; Stephen C. Jacobsen; notice of allowance dated Jul. 25, 2012.

U.S. Appl. No. 12/350,693, filed Jan. 8, 2009; Stephen C. Jacobsen; notice of allowance dated Sep. 20, 2012.

Mehling, et al.; "A Minimally Invasive Tendril Robot for In-Space Inspection"; Biomedical Robotics and Biomechatronis, 2006.

U.S. Appl. No. 13/481,631, filed May 25, 2012; Ralph W. Pensel; notice of allowance dated Sep. 24, 2012.

U.S. Appl. No. 12/814,304, filed Jun. 11, 2010; Stephen C. Jacobsen; office action dated Nov. 13, 2012.

U.S. Appl. No. 12/117,233, filed May 8, 2008; Stephen C. Jacobsen; office action dated Nov. 23, 2012.

Celaya et al; Control of a Six-Legged Robot Walking on Abrupt Terrain; Proceedings of the 1996 IEE International Conference on Robotics and Automation, Minneapolis, Minnesota; Apr. 1996; 6 pages.

Burg et al; Anti-Lock Braking and Traction Control Concept for All-Terrain Robotic Vehicles; Proceedings of the 1997 IEE International Conference on Robotics and Automation; Albuquerque, New Mexico; Apr. 1997; 6 pages.

U.S. Appl. No. 12/117,233; filed May 8, 2008; Stephen C. Jacobsen. office action dated Nov. 23, 2012.

U.S. Appl. No. 12/171,146; filed Jul. 10, 2008; Stephen C. Jacobsen; office action dated Mar. 6, 2013.

\* cited by examiner

TWO-DIMENSIONAL LAYOUT FOR USE IN A COMPLEX STRUCTURE

RELATED APPLICATIONS

This application is a divisional of U.S. patent application Ser. No. 12/151,730 (now U.S. Pat. No. 8,002,716), filed May 7, 2008, and entitled "Method for Manufacturing a Complex Structure", which claims the benefit of U.S. Provisional Application Ser. No. 60/928,149, filed May 7, 2007, and entitled, "Method for Manufacturing a Complex Structure," each of which are incorporated by reference herein in their entirety.

FIELD OF THE INVENTION

The present invention relates generally to complex structures, such as robotic devices or medical devices, and more particularly to a method for manufacturing a complex structure.

BACKGROUND OF THE INVENTION AND RELATED ART

Complex structures, such as high aspect ratio structures, or guidewires, have long been used in medical, industrial, and other fields for insertion into a lumen or conduit or other similar ducted structure for one or more purposes. For example, in the medical field an endoscope is a medical instrument for visualizing the interior of a patient's body. Endoscopes can be used for a variety of diagnostic and interventional procedures, including, colonoscopy, bronchoscopy, thoracoscopy, laparoscopy, and video endoscopy. The use of guidewires in applications other than those for medical purposes include any applications in which it is desirable to inspect, repair, position an object such as tools within, or otherwise facilitate travel into and through a tube, pipe, or other similar conduit for one or more purposes.

As is known, a guidewire having a relatively low resistance to flexure yet relatively high torsional strength is most desirable. Stated differently, it is often desired that certain portions or all of a guidewire have lateral flexibility characteristics as well as pushability (the ability to push) and torquability (the ability to torque or twist the guidewire with sufficient torsional or rotational stiffness) characteristics. As the guidewire is advanced into the anatomy, internal frictional resistance resulting from the typically numerous turns and attendant surface contacts, decreases the ability to turn the guidewire and to advance the guidewire further within the luminal space. This, in turn, may lead to a more difficult and prolonged procedure, or, more seriously, failure to access the desired anatomy at the target location and thus a failed procedure.

A guidewire with high flexibility helps overcome the problems created by this internal resistance. However, if the guidewire does not also have good torque characteristics (torsional stiffness), the user will not be able to twist the proximal end in order to rotate the distal tip of the guidewire to guide its advance as required. Indeed, depending upon its use, a guidewire may be required to have adequate torsional strength over its length to permit steering of the distal tip portion into the correct vessel branches by axially rotating the proximal end. The guidewire, and especially the distal end portion, may be required to be sufficiently flexible so that it can conform to the acute curvature of the vessel network. Additionally, a guidewire with compression strength may be needed, wherein the compression strength is suitable for pushing the guidewire into the vessel network without collapsing.

Other complex structures include hyper redundant robotic structures, such as serpentine or snake robots capable of mimicking the locomotion of a snake. Such robotic devices may be configured to perform various functions, such as to negotiate complicated three-dimensional spaces including pipes, stairs, vertical piles of rubble, etc. These robotic devices commonly comprise a plurality of actuated jointed segments that are movable with respect to one another in various degrees of freedom via a plurality of servo or other similar valves. In addition, they may be equipped with various devices, such as cameras, sensors, and other technology depending upon their intended use.

Current methods of fabricating or manufacturing small, three-dimensional complex structures requires assembling the structure one segment at a time. Any components or systems to be incorporated into one or more segments must also be assembled thereon as the segments are being put together. This rudimentary method is complicated even further when various electrical connections are desired to be incorporated to provide power and electrical signal carrying capabilities to the complex structure. Such manufacturing methods do not lend the complex structure to mass production, thus increasing the cost of each structure and the time to production.

SUMMARY OF THE INVENTION

In light of the problems and deficiencies inherent in the prior art, and in accordance with the invention as embodied and broadly described herein, the present invention features a method for manufacturing a complex structure from a two-dimensional layout, the method comprising: (a) obtaining a support plate having a pre-determined, patterned recess formed in a surface thereof; (b) depositing a first series of individual flexible interconnects into the recess, the flexible interconnects being aligned parallel to one another in a common plane and supported by the support plate; (c) adhering, such as with adhering means, at least one rigid member to each of the flexible interconnects of the first series; (d) adhering, such as with adhering means, a second series of individual flexible interconnects to the rigid members to form a plurality of stations, wherein each of the second series of flexible interconnects is adhered to two rigid members of adjacent flexible interconnects of the first series, the flexible interconnects of the second series being formed perpendicular to the flexible interconnects of the first series; (e) curing the adhering means to form an assembled, layered structure; (f) removing the layered structure from the support plate; and (g) folding, systematically, the layered structure on itself and causing at least some of the stations to be supported about a central spine in a segmented manner.

In one exemplary embodiment, the flexible material may be a metalized polyimide film, i.e. Kapton, enabling the rigid members to be electrically interconnected, as well as allowing the complex structure to electrically communicate with an electronic source, such as a computer or other electronic device or system, for one or more purposes.

The rigid members themselves may comprise one or more on-board systems that may be incorporated into the two-dimensional layout used to form the complex structure. In one exemplary embodiment, an on-board system may enable the rigid members to function as intelligent performance stations. The rigid members may comprise computer chips or silicon substrates with circuitry and data processing/storing components thereon. In this case, each rigid member may be networked or multiplexed together via the metalized polyimide film material interconnecting the various stations. Nodes, or output stations, may also be utilized between the various stations, which nodes may also electrically communicate with the various stations via the metalized polyimide film interconnects.

In another exemplary embodiment, an on-board system may enable the rigid members to function as mechanical or fluid or electro-mechanical performance stations. For example, the rigid members may support actuators and valves operable with the actuators, which actuators and valves may be in fluid communication with a hydraulic bus running parallel to the central spine In essence, the present invention contemplates any component or on-board system being incorporated into the layered, two-dimensional layout used to ultimately form the complex structure.

The present invention also features a method for manufacturing a complex structure similar to the one summarized above, only the flexible material comprises a single piece design, rather than a plurality of individual pieces. In this embodiment, additional steps of trimming or cutting may be necessary to remove a portion of the flexible material prior to or as the rigid members are being supported about and secured to the central spine.

The present invention further features a complex structure formed from a two-dimensional layout, wherein the complex structure comprises: (a) a central spine; (b) a plurality of stations situated about and supported on the central spine; and (c) a flexible interconnect extending between each of the stations, the flexible interconnect being configured to operably interconnect the stations, and the stations being formed by adhering the flexible interconnects to a plurality of rigid members within a two-dimensional layout and then folding the rigid members and the flexible interconnects, once attached, about one another while threading these onto the central spine.

BRIEF DESCRIPTION OF THE DRAWINGS

The present invention will become more fully apparent from the following description and appended claims, taken in conjunction with the accompanying drawings. Understanding that these drawings merely depict exemplary embodiments of the present invention they are, therefore, not to be considered limiting of its scope. It will be readily appreciated that the components of the present invention, as generally described and illustrated in the figures herein, could be arranged and designed in a wide variety of different configurations. Nonetheless, the invention will be described and explained with additional specificity and detail through the use of the accompanying drawings in which:

FIG. 3-B illustrates a detailed view of a single rigid member shown in FIG. 3-A as deposited over a flexible interconnect;

DETAILED DESCRIPTION OF EXEMPLARY EMBODIMENTS

Figure 1:
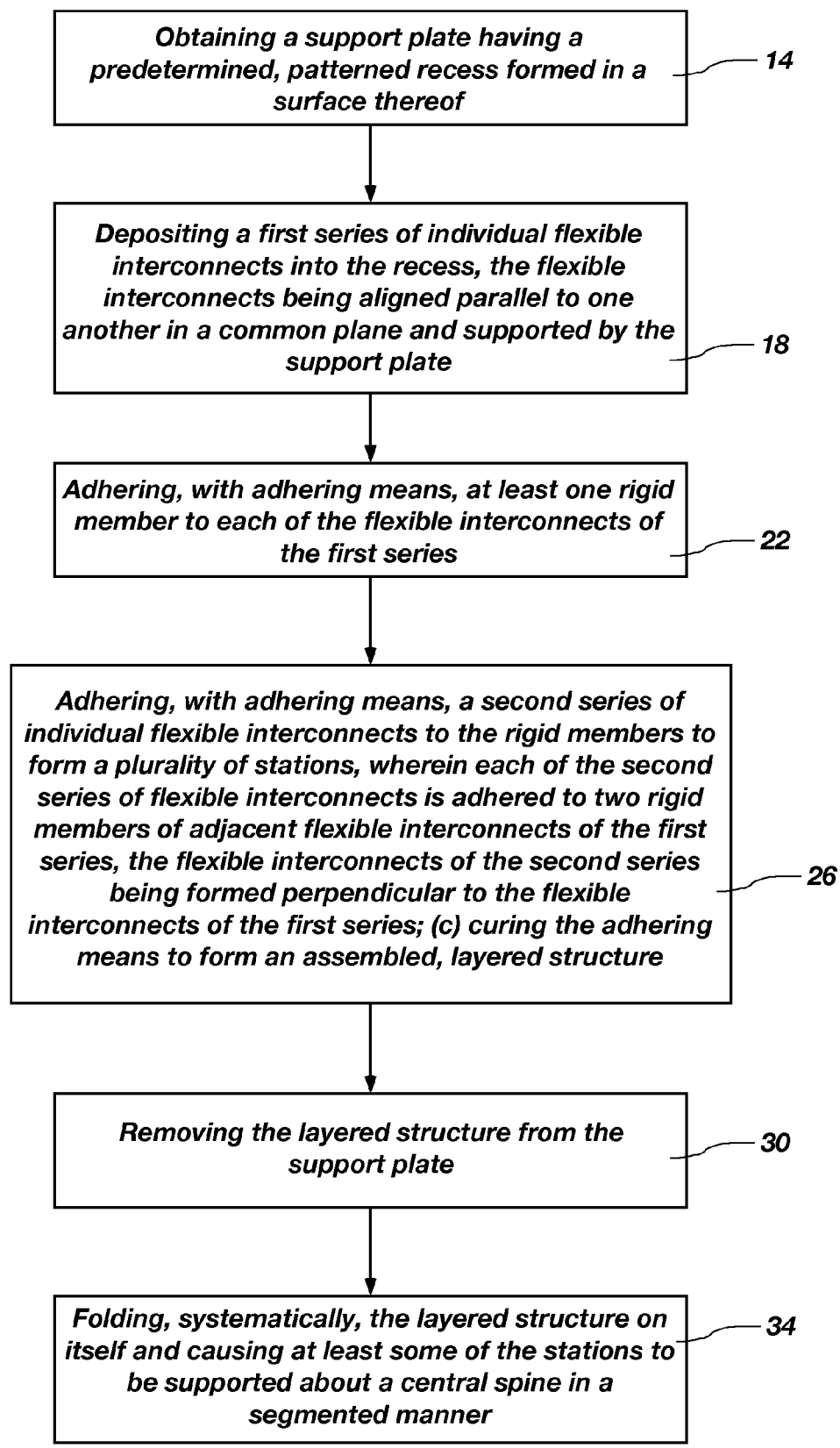
FIG. 1 illustrates a flow diagram of a method of manufacturing a complex structure from a two-dimensional layout, according to one exemplary embodiment of the present invention.

The following detailed description of exemplary embodiments of the invention makes reference to the accompanying drawings, which form a part hereof and in which are shown, by way of illustration, exemplary embodiments in which the invention may be practiced. While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention, as represented in FIGS. 1 through 7, is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

The following detailed description and exemplary embodiments of the invention will be best understood by reference to the accompanying drawings, wherein the elements and features of the invention are designated by numerals throughout.

Generally speaking, the present invention describes a method for manufacturing a three-dimensional, complex structure using a two-dimensional layout, wherein the complex structure comprises a plurality of performance stations that are preferably segmented, such as intelligence and/or actuation or electro-mechanical stations. Unlike prior related methods of manufacturing, the present invention method accomplishes all of the assembly of the complex structure, such as mechanical and electrical interconnects, in only a few steps, wherein the complex structure is then formed. As such, the present invention lends itself particularly well to mass fabrication of complex structures.

The present invention method may be used to manufacture a variety of different types of complex structures. For instance, one generic type of complex structure may comprise various electro-mechanical structures, such as robotic devices, medical devices, and others. In one particular exemplary embodiment, the complex electro-mechanical structure may comprise an electro-mechanical guidewire configured for use in various applications and in various industries, such as the medical or robotic industries, wherein the electro-mechanical guidewire comprises a plurality of performance stations having one or more on-board systems capable of performing various intelligent (e.g., data processing, signal receiving, signal transmitting, sensing, etc.), mechanical (e.g., actuation, locomotion), valving, or other functions. Although this particular application or embodiment is set forth and discussed in detail herein, such a structure should not be construed as limiting in any way. Indeed, as one skilled in the art will recognize, a variety of different types of complex structures may be formed using the manufacturing method as described or presented herein.

Preliminarily, the term "station," as used herein, shall be understood to mean a rigid or semi-rigid member having at least one flexible interconnect connected thereto. A complex structure according to the present invention will typically comprise a plurality of stations, some of which may be support stations, performance stations, or both.

The term "performance station," as used herein, shall be understood to mean a rigid member configured with or supporting thereon one or more on-board systems. Performance stations may include intelligent performance stations, electrical performance stations, mechanical performance stations, actuation performance stations, information gathering performance stations, valving and pumping performance stations, electro-mechanical performance stations, and others. On-board systems may include circuitry, circuit boards, actuators, valves, sensors, transmitters, cameras, locomotion devices or systems, or any combination of these. Those skilled in the art will recognize others.

The terms "intelligent" or "intelligence," as used herein, shall be understood to describe those on-board features or components of the present invention having the capability to perform one or more data processing functions. This may include the capability to receive, process, send, and store electronic signals.

The present invention provides several significant advantages over prior related methods of manufacturing or fabricating complex structures, some of which are recited here and throughout the following more detailed description. Each of the advantages recited herein will be apparent in light of the detailed description as set forth, with reference to the accompanying drawings. These advantages are not meant to be limiting in any way. Indeed, one skilled in the art will appreciate that other advantages may be realized, other than those specifically recited herein, upon practicing the present invention.

With reference to FIG. 1, illustrated is a block diagram depicting a method for manufacturing or fabricating a complex structure, according to one exemplary embodiment of the present invention. As shown, the method comprises the following steps. Step 14 comprises obtaining a support plate having a pre-determined, patterned recess formed in a surface thereof. Step 18 comprises depositing a first series of individual flexible interconnects into the recess, the flexible interconnects being aligned parallel to one another in a common plane and supported by the support plate. Step 22 comprises adhering, with adhering means, at least one rigid member to each of the flexible interconnects of the first series. Step 26 comprises adhering, with adhering means, a second series of individual flexible interconnects to the rigid members to form a plurality of stations, wherein each of the second series of flexible interconnects is adhered to two rigid members of adjacent flexible interconnects of the first series, the flexible interconnects of the second series being formed perpendicular to the flexible interconnects of the first series. Step 30 comprises curing the adhering means to form an assembled, layered structure. Step 34 comprises removing the layered structure from the support plate and folding, systematically, the layered structure on itself and causing at least some of the stations to be supported about a central spine in a segmented manner. In an alternative embodiment, the flexible interconnects on either side of the rigid members may comprise a single strand of material rather than a plurality of individual pieces.

Figure 2:
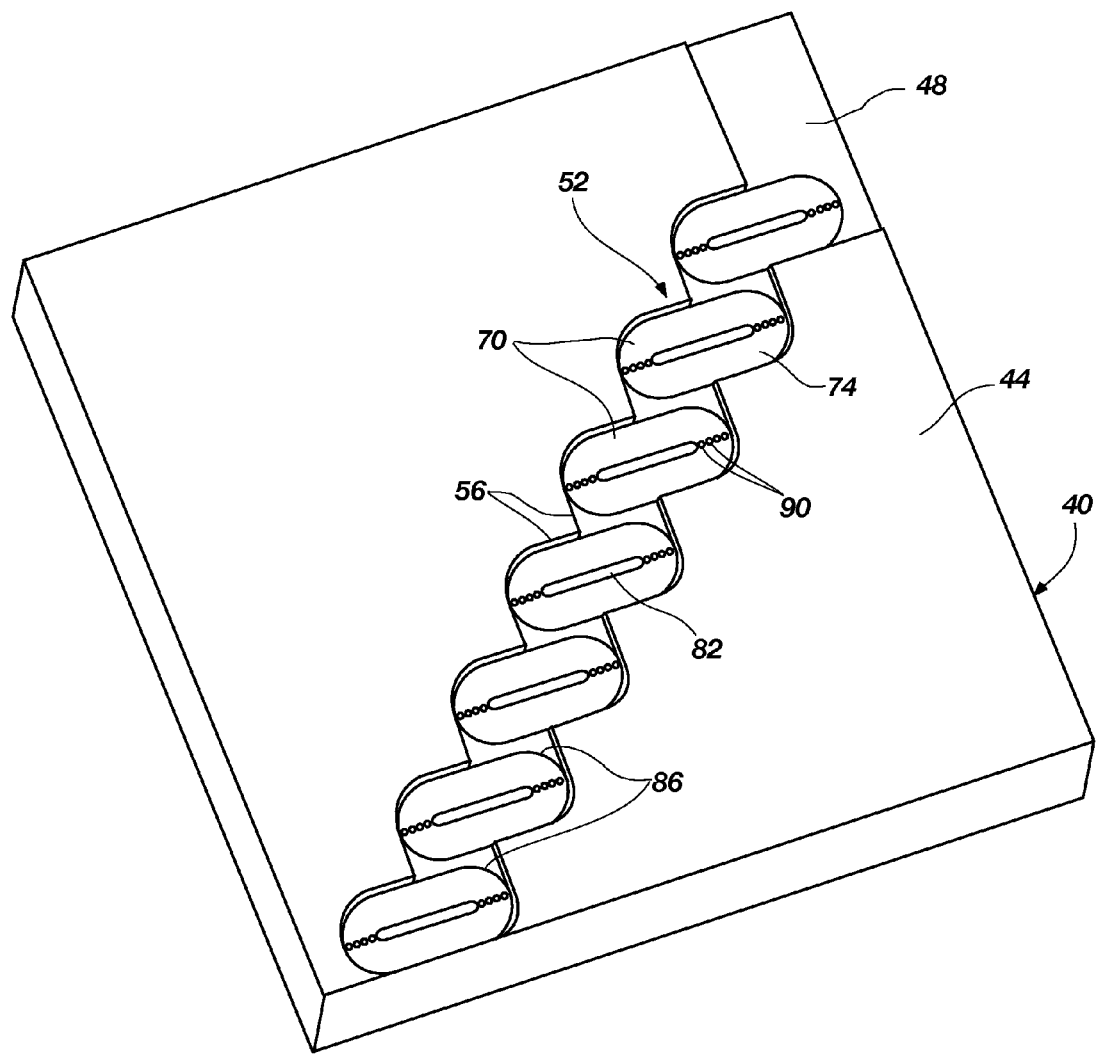
FIG. 2 illustrates a perspective diagram of a support plate having a recessed pattern formed therein that is capable of receiving a first series of flexible interconnects in a pre-determined arrangement.

FIGS. 2-6 illustrate the steps recited above as applied to the manufacture of a specific exemplary type of complex structure. More specifically, FIGS. 1-6 illustrate the various components and elements involved in manufacturing a segmented complex structure in accordance with the steps recited above, wherein the complex structure is in the form of a guidewire having a plurality of performance stations configured with the ability to support a plurality of on-board systems capable or performing one or more mechanical, electrical, electro-mechanical, or other functions. With specific reference to FIG. 2, illustrated is a support plate 40 having an upper surface 44 and a recessed portion 48 formed in the upper surface 44. The support plate 40 effectively functions as a template having a pattern 52 for laying out, in a two-dimensional manner, the various components used to make up the complex structure. The recessed portion 48 conforms to or comprises the desired pattern 52. The recessed portion 48 and pattern 52 formed in the support plate 40 further functions to properly align each of the components as they are laid out by providing boundaries. As shown, the boundary 56 of the pattern 52 comprises the edges of the recessed portion 48. In another exemplary embodiment, the boundary may be provided by a build-up extending above the surface 44 of the support plate 40, wherein the components of the complex structure are laid upon the surface 44 rather than within a recessed portion.

The size and geometry of the particular pattern 52 may vary depending upon the type or configuration of complex structure desired to be produced. In the exemplary embodiment shown, the pattern comprises a step-like configuration, with a plurality of similarly sized rectangular shaped segments with rounded ends arranged in an overlapping manner one with another. Obviously, other patterns may be formed in the support plate 40 as will be recognized by those skilled in the art. In addition, the support plate 40 may be used to form a continuous complex structure or various segments of a complex structure. In the embodiment shown, and in light of the high aspect ratio of guidewires, the support plate 40 is most likely used to form various segments of a complex guidewire structure due to its small size and the relatively small number of components able to be laid out about the support plate 40, as shown. Of course, the support plate 40 may comprise larger sizes capable of facilitating the formation of much larger complex structures or segments.

The recessed portion 48 may be configured to accommodate and support the layout of components of various sizes. In one aspect, the recessed portion 48 may comprise any depth (or alternatively, any buildups may comprise any height) or varying depths (or alternatively varying buildup heights), depending upon the complex structure to be formed. For example, the recess 48 may not be required to be as deep to accommodate and support those components used to make up a simple guidewire structure having no on-board systems, as opposed to the depth that may be needed to accommodate and support a complex structure having one or more on-board components, such as a mechanical actuator or other system or device.

The support plate 40 may comprise any metal or non-metal material capable of supporting the various complex structure components in place during the manufacturing process. And, as indicated above, the support plate 40 may be configured to comprise any size and geometric configuration.

In forming the complex guidewire structure, a first series or set of individual flexible interconnects 70 are laid out in a common plane within the recess 48. In other words, the flexible interconnects 70 are configured to be usable within a two-dimensional layout. Each flexible interconnect 70 is further configured to provide the foundation for receiving all other components, which are also configured to be usable within a two-dimensional layout. The flexible interconnects 70 function to operably interconnect one or more rigid members or stations of the complex guidewire structure. The interconnection between the rigid members or stations may provide multiple functions. For example, the interconnects may be configured to provide mechanical support, or they may be configured to comprise an electrical interconnection element, depending upon the makeup or configuration of the material used, or both of these. In any event, the interconnects 70 between the rigid members are intended to be flexible in order to facilitate the various movements and functions of the segments and stations during use of the guidewire structure. For example, it may be desired to configure the complex guidewire structure so that the rigid members or stations are able to twist, bend, extend, compress, or otherwise move with respect to one another. By being flexible, the interconnects 70 are able to likewise move with the rigid members without sacrificing functionality. This is particularly advantageous when the flexible interconnects 70 operate to carry electrical current or signals. Thus, the present invention contemplates a variety of interconnect combinations being possible.

Each of the flexible interconnects 70 comprise a pre-determined two-dimensional size and shape depending upon the particular complex structure to be formed. As such, the pattern 52 formed in the support plate 40 comprises a corresponding size and shape to accommodate or receive the flexible interconnects 70, in two-dimensional form. In other words, the flexible interconnects 70 each comprise a two-dimensional size and shape that allows them to be properly supported within the pattern 52 of the support plate 40 during manufacturing. In keeping with the exemplary embodiment, each of the flexible interconnects 70 comprise a two-dimensional form with a first surface 74, a second surface (not shown), a slot or slotted portion 82, which purpose or function will be discussed in detail below, and a perimeter 86. In addition, the flexible interconnects 70 each comprise a rectangular shape with rounded ends, as this shape will allow them to take on the desired configuration in the three-dimensional complex structure when formed.

As shown in this particular two-dimensional layout, the first series of flexible interconnects 70 are all laid out so that they are oriented in the same direction and in a parallel manner with respect to one another. Each flexible interconnect 70 is laterally offset from the other a pre-determined distance. Each interconnect 70 is also offset from the other a pre-determined distance lengthwise (which distance is shown as substantially half the length of a flexible interconnect). As such, the various interconnects 70 are positioned in a step-like manner with respect to one another (as dictated by pattern 52). The recessed portion 48 formed in the pattern 52 is configured to allow the flexible interconnects 70 to nest therein. As indicated above, the support plate 40 may take on any configuration as long as it is capable of supporting the flexible interconnects 70 in a proper orientation.

The flexible interconnects 70 may comprise any suitable material capable of flexing, such as plastic, polymer, shape memory alloy and polyimide film. In the embodiment shown, the flexible interconnects 70 each comprise thin-layer strips of metalized polyimide material, which material is commonly known in the art. Each piece of metalized polyimide film comprises a plurality of electrical connectors 90 configured to electrically connect the metalized polyimide film to adjacent segments or stations and to other components making up the complex guidewire structure, such as one or more electronic on-board components (e.g., data or signal processing system). The metalized polyimide film facilitates the carrying of electrical current or signals along the length of the complex structure from segment to segment or station to station, which electrical signals may be used for a variety of purposes, such as to power certain components of on-board systems located on the various segments or stations of the complex guidewire structure. Moreover, if desired, by providing electrical intercommunication, the various rigid members or stations of the complex guidewire structure, or individual stations, may be addressed and networked together. In addition, the complex guidewire structure may be multiplexed, allowing any number of stations to communicate with one another and/or with various input and output devices, such as a computer. The concepts of addressing, networking, and multiplexing are discussed in greater detail below.

As mentioned above, in another exemplary embodiment, the flexible interconnects may comprise a single strand of material, such as a single strand of metalized polyimide film, sized and shaped to fit within the pattern 52 in a similar manner as the individual flexible interconnect pieces. The same is true for the flexible interconnects on the opposite side of the rigid members, as discussed below. The single strand flexible interconnect will still comprise the necessary slots or apertures to accommodate a central spine, as well as any electrical connectors, conduits, etc. desired.

Figure 3:
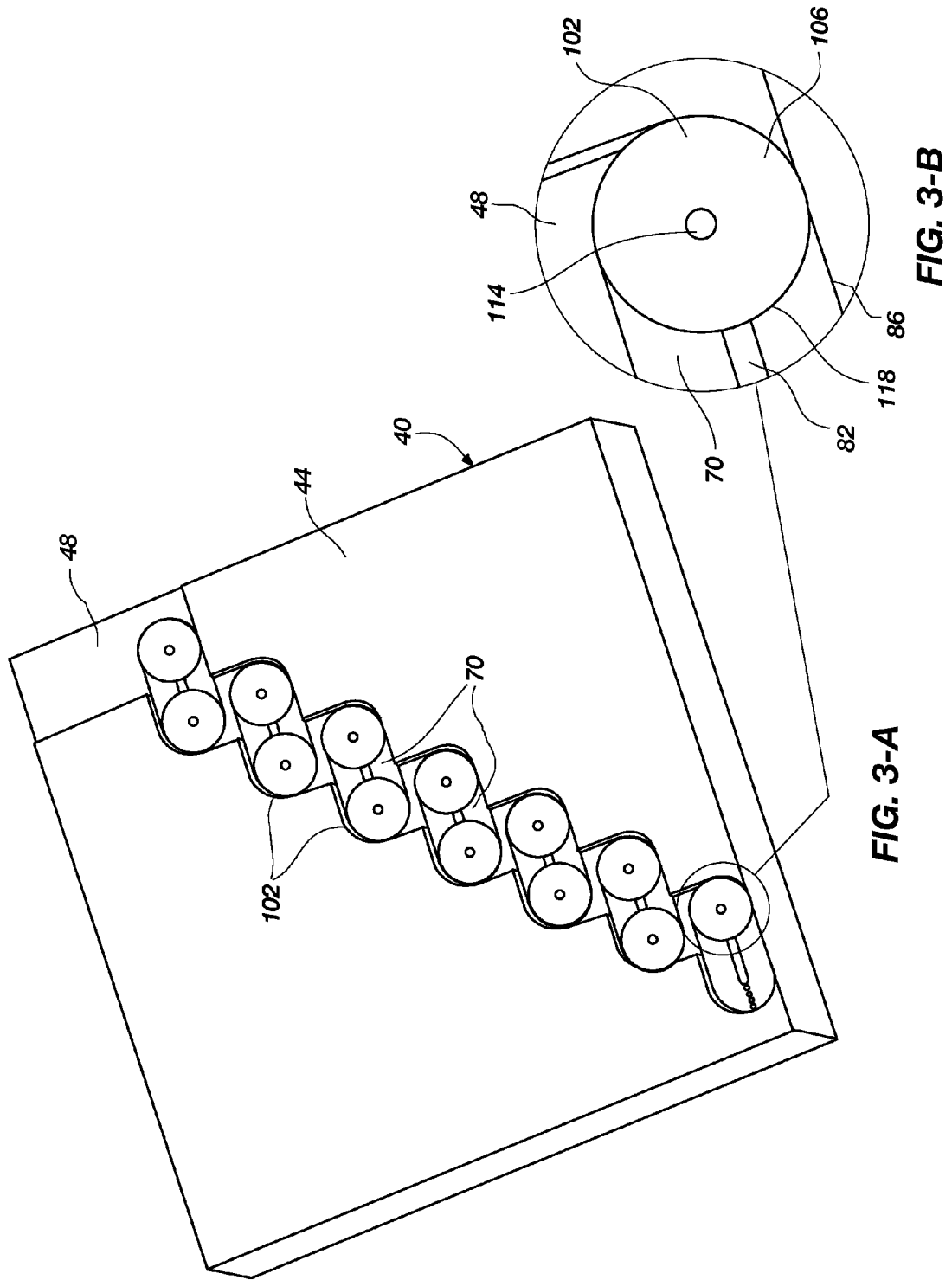
FIG. 3-A illustrates a perspective view of the support plate of FIG. 2 having a plurality of rigid members deposited in pre-determined arrangement over the flexible interconnects.

With reference to FIGS. 3-A and 3-B, shown are a plurality of rigid members 102 disposed within the recessed portion 48 of the upper surface 44 of the support plate 40, and positioned or aligned over the ends of each of the flexible interconnects 70. The rigid members 102 are comprised of circular discs having an first surface 106, a second surface (not shown), an aperture 114 centrally formed therein, and a perimeter 118 defining a circle.

Prior to disposing the rigid members 102 over the flexible interconnects 70, adhering means, such as an adhesive or solder paste, is applied to the areas where the rigid members 102 will be attached to the flexible interconnects 70, or where electrical connectivity is required or desired. The adhering means functions to operably attach the rigid members 102 to the flexible interconnects 70, such as to electrically connect the rigid member with the electrical components of the flexible interconnect (e.g., the electrical connectors and/or electrical conduits in the polyimide material). In some embodiments, a suitable adhering means may be used to electrically connect the electrical connectors in the flexible interconnect 70 (see electrical connectors 90 in FIG. 2) to the rigid members 102, thus allowing the rigid members 102 to carry an electrical current through one or more electrical conduits supported thereon, and to electrically connect one or more on-board systems, if desired.

The rigid members 102 may comprise various types of materials, namely those selected from both metals and non-metals. In one exemplary embodiment, the rigid members 102 may be comprised of computer chips or silicon substrates with circuitry and data processing/storing components thereon, thus providing the ability for the rigid member to function as an intelligent performance station, such as a circuit board. In another exemplary embodiment, the rigid members 102 may be comprised of metal where additional support capabilities are needed. Indeed, various combinations of material are also contemplated. In essence, the rigid members 102 are configured to function as support stations, and where appropriate, performance stations (e.g., intelligent, mechanical, etc.), that are independent of one another except through their interconnection via the flexible interconnects 70.

Other than circular, one skilled in the art will recognize that the rigid member 102 may comprise other shapes and sizes, depending upon the particular design of the complex structure being formed.

The rigid members 102 preferably comprise a diameter that is at least as long as the flexible interconnects 70 are wide. In addition, the rigid members 102 may comprise a cross-section selected from the group consisting of a plane geometry shape and an arbitrary shape, as known in the art. However, this is not intended to be limiting as other sizes may be useful. In the embodiment shown, the rigid members 102 comprise a diameter that is the same or substantially the same length as the width of the flexible interconnects 70. In addition, the radius of the rounded ends of the flexible interconnects 70 are the same or substantially the same as the radius of the rigid members 102, thus allowing a portion of their perimeters 86 and 118, respectively, to match. The rigid members 102 are positioned over the ends of the flexible interconnects 70, one at each end, thus leaving a small gap between the two rigid members 102 on any given flexible interconnect, and thus leaving a portion of the slot 82 exposed, or not covered. In addition, adjacent rigid members 102 located on adjacent flexible interconnects are also separated a given distance, for the purpose of leaving exposed a portion of the slot of the second series of flexible interconnects, as discussed below.

Figure 4:
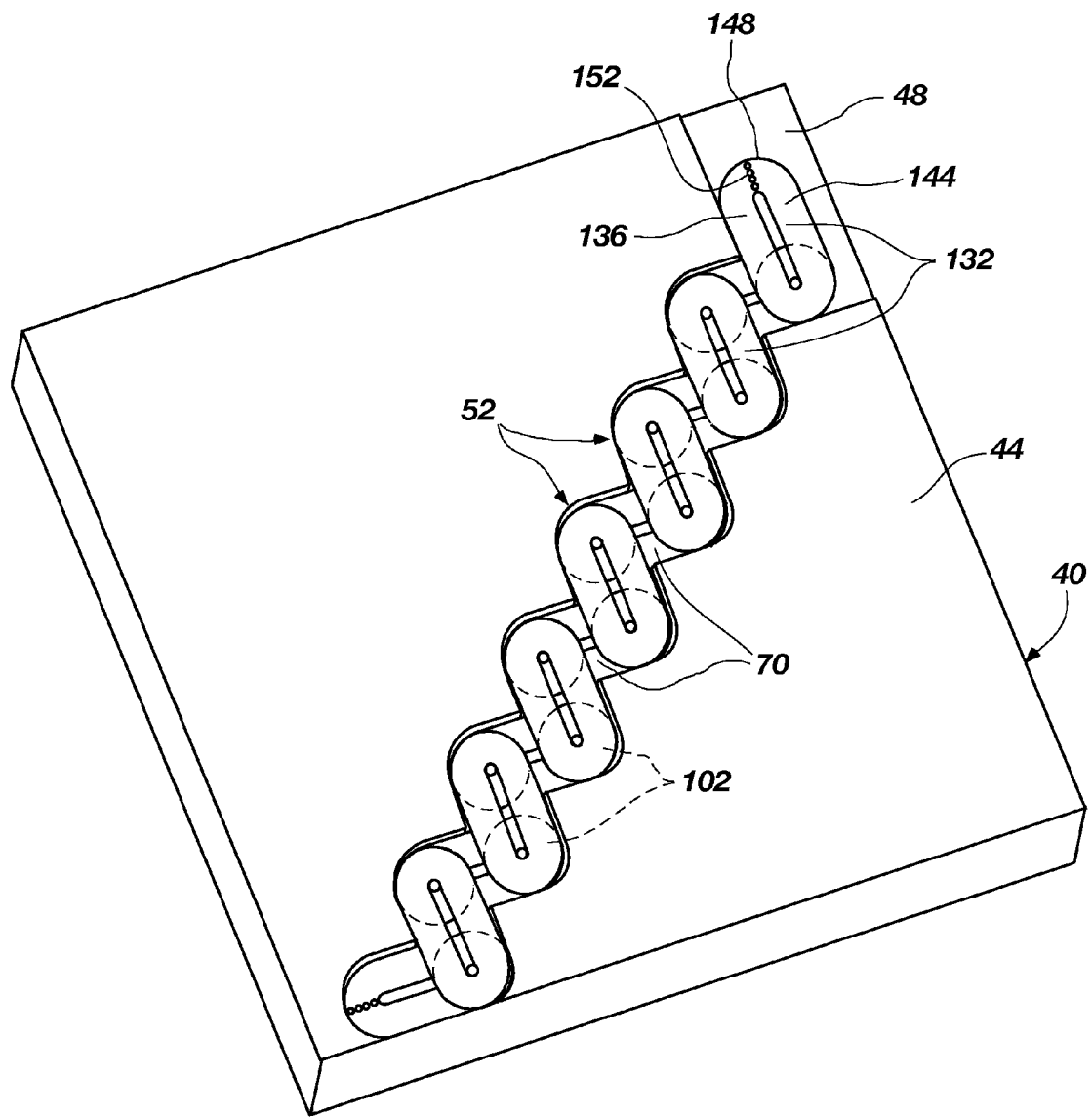
FIG. 4 illustrates a perspective view of the support plate of FIG. 2 having a second series of flexible interconnects deposited over the rigid members in a pre-determined arrangement, whereupon curing, the assembly forms a plurality of stations.

Once all of the rigid members 102 are in place and adhering means has been applied, the process of forming a complex structure involves disposing a second series of flexible interconnects over the first series and the rigid members, and aligning or positioning these in their proper place. With reference to FIG. 4, illustrated is a plurality of a second series of flexible interconnects 132 as overlaid upon the rigid members 102. As shown, the second series of flexible interconnects 132 are all laid out so that they are oriented in the same direction and in a parallel manner with respect to one another, but perpendicular or orthogonal to the first series of flexible interconnects 70. Each flexible interconnect 132 is laterally offset from the other a pre-determined distance. Each interconnect 132 is also offset from the other a pre-determined distance lengthwise (which distance is shown as substantially half the length of a flexible interconnect). As such, the various first and second series of flexible interconnects 70 and 132 are positioned in a step-like manner with respect to one another (as dictated by pattern 52). As with the first series, the recessed portion 48 formed in the pattern 52 is configured to support the second series of flexible interconnects 132 and to allow the second series of flexible interconnects 132 to nest therein as overlaid upon the rigid members 102.

The second series of flexible interconnects 132 are similar to the first series in that they comprise a two-dimensional form with a first surface 136, a second surface (not shown), a slot or slotted portion 144, and a perimeter 148. In addition, the flexible interconnects 132 each comprise a rectangular shape with rounded ends, as this shape will allow them to take on the desired configuration in the three-dimensional complex structure when formed. The second series of flexible interconnects 132 may also comprise electrical connectors 152, similar to and that function as those disposed on the first series of flexible interconnects. The second series of flexible interconnects 132 may comprise any size, shape, material, etc. as discussed above with respect to the first series of flexible interconnects.

Prior to laying out and aligning or positioning the second series of flexible interconnects 132, adhering means, such as an adhesive or solder paste, is applied to the areas where the rigid members 102 will be attached to the flexible interconnects 132, or where electrical connectivity is required or desired. The adhering means functions to attach the rigid members 102 to the second series of flexible interconnects 132 in the same manner as discussed above. As such, the rigid members 102, with their flexible interconnect counterparts, become defined stations to be disposed and situated in their proper place to make up the complex structure.

Moreover, and also prior to laying out and aligning the second series of flexible interconnects 132, various on-board systems or components or devices may be laid out and attached to one or more of the rigid members 102. For example, in the event a particular rigid member or station is to function as a performance station, such as an intelligent performance station in the form of a computer chip, all of the necessary data processing, data storage, and circuitry may be applied to the rigid member 102 at this time. Other on-board systems may include valving systems, micro cameras, actuators, deployment systems, etc. For instance, the on-board systems may enable the rigid members to function as mechanical or fluid or electro-mechanical performance stations. For example, the rigid members may support actuators and valves operable with the actuators, which actuators and valves may be in fluid communication with a hydraulic bus running parallel to the central spine. In essence, the present invention contemplates any component, system or device functioning an on-board system and being incorporated into the layered, two-dimensional layout used to ultimately form the complex structure.

The on-board systems, depending upon their type and components, are operably coupled or connected to the rigid members and/or the flexible interconnects. For instance, in the event of a rigid member being configured with one or more data processing components, these components are electrically connected to the electrical components in the flexible interconnects, such as the electrical connectors and conduits (e.g., those present on the polyimide film), and also any electrical components located on the rigid members required for operation of the data processing components. Once electrically connected, the data processing components can perform their intended function of receiving, transmitting, and/or storing electrical signals received. The flexible interconnects provide an uninterrupted conduit for electrical signals to be transmitted from any one station to any other station in the complex structure and from any input device (such as a computer) in communication with the complex structure to any station.

In addition, the complex structure may comprise one or more nodes existing between the stations. Exemplary nodes include actuating devices or systems, cameras, sensors, transmitters, etc.

Once all of the components discussed above are properly positioned and attached to one another, the adhering means may then be cured to complete the formation of the two-dimensional assembly. One exemplary curing process comprises covering the layered two-dimensional structure with a top plate and exposing the same to a pre-determined temperature for a pre-determined duration of time. Other curing procedures used to cure the adhering means will be apparent to those skilled in the art.

Figure 5:
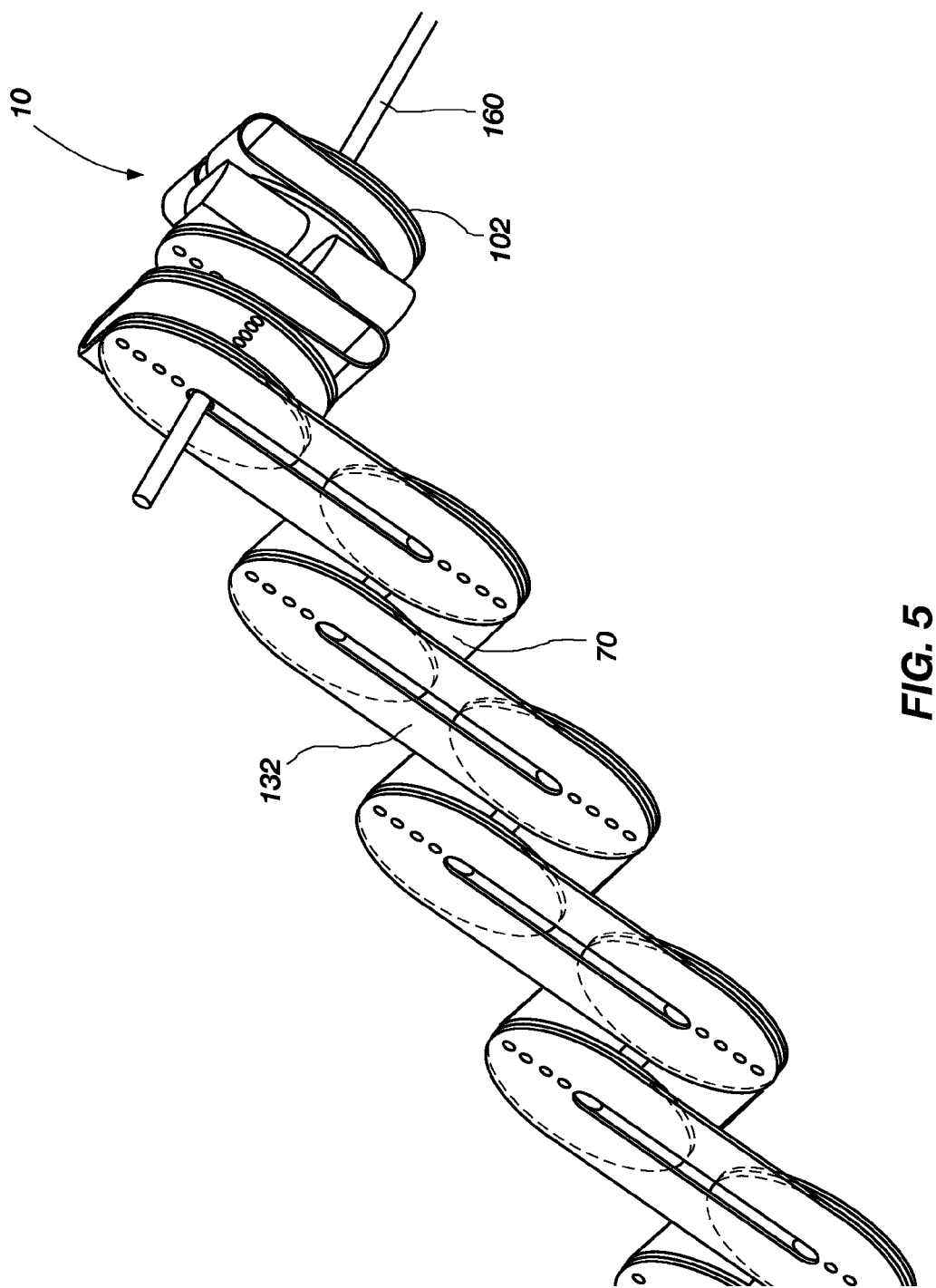
FIG. 5 illustrates the resulting layered, two-dimensional assembly as being folded about itself and threaded onto a central spine, thus forming the three-dimensional complex structure.

With reference to FIG. 5, once the adhering means is cured, the two-dimensional assembly is removed from the support plate and threaded along a central spine 160 by systematically folding the flexible interconnects 70 and 132, and therefore the rigid members 102, about one another. Upon folding the interconnects, the central spine 160 is inserted through the portion of the slots in each of the flexible interconnects 70 and 132 left exposed between each of the rigid members 132, as well as the apertures formed in the rigid members 102, as shown. The flexible interconnects 70 and 132 are preferably folded to locate the flexible interconnects inside of or between each corresponding rigid member as supported about the central spine. This process is continued until the each of the rigid members 102 is situated about the central spine 160, as stations, with the flexible interconnects spanning therebetween. Although not required, once in place, the rigid members 102 may be attached or fixed to the central spine 160 at their appropriate locations using any known attachment means.

The central spine 160 may comprise any type of support member, such as a compression member, capable of supporting the rigid members 102 in place. Preferably, the central spine 160 will also be capable of providing the complex structure with torquability, pushability, and flexing characteristics.

The resulting structure comprises a three-dimensional complex structure 10 formed from the above-described two-dimensional layout. Each of the rigid members 102 function as or provide a station capable of performing one or more tasks. Indeed, as discussed herein, a station may be a simple support station contributing to the overall support of the complex structure, or a station may function as a performance station, wherein one or more on-board systems is configured to perform an intelligent (e.g., data processing, signal receiving, signal transmitting, sensing, etc.) function, a mechanical function (e.g., actuation, locomotion), a valving function, or some other function as recognized by those skilled in the art. Advantageously, the stations of the complex structure are capable of supporting one or more operable on-board systems, as well as being able to receive and send signals, information, or other items to any other station in the complex structure, to a node, or to a computer via the flexible interconnect and resulting electrical interconnection between the stations.

The complex structure is also capable of unique movements. Indeed, the complex structure may be configured to bend, torque, twist, extend, etc. to perform its intended function. One exemplary complex structure that may be formed using the present invention method may be similar to, in both form and function, a complex guidewire. Another exemplary type of complex structure may comprise a serpentine robot.

Figure 6:
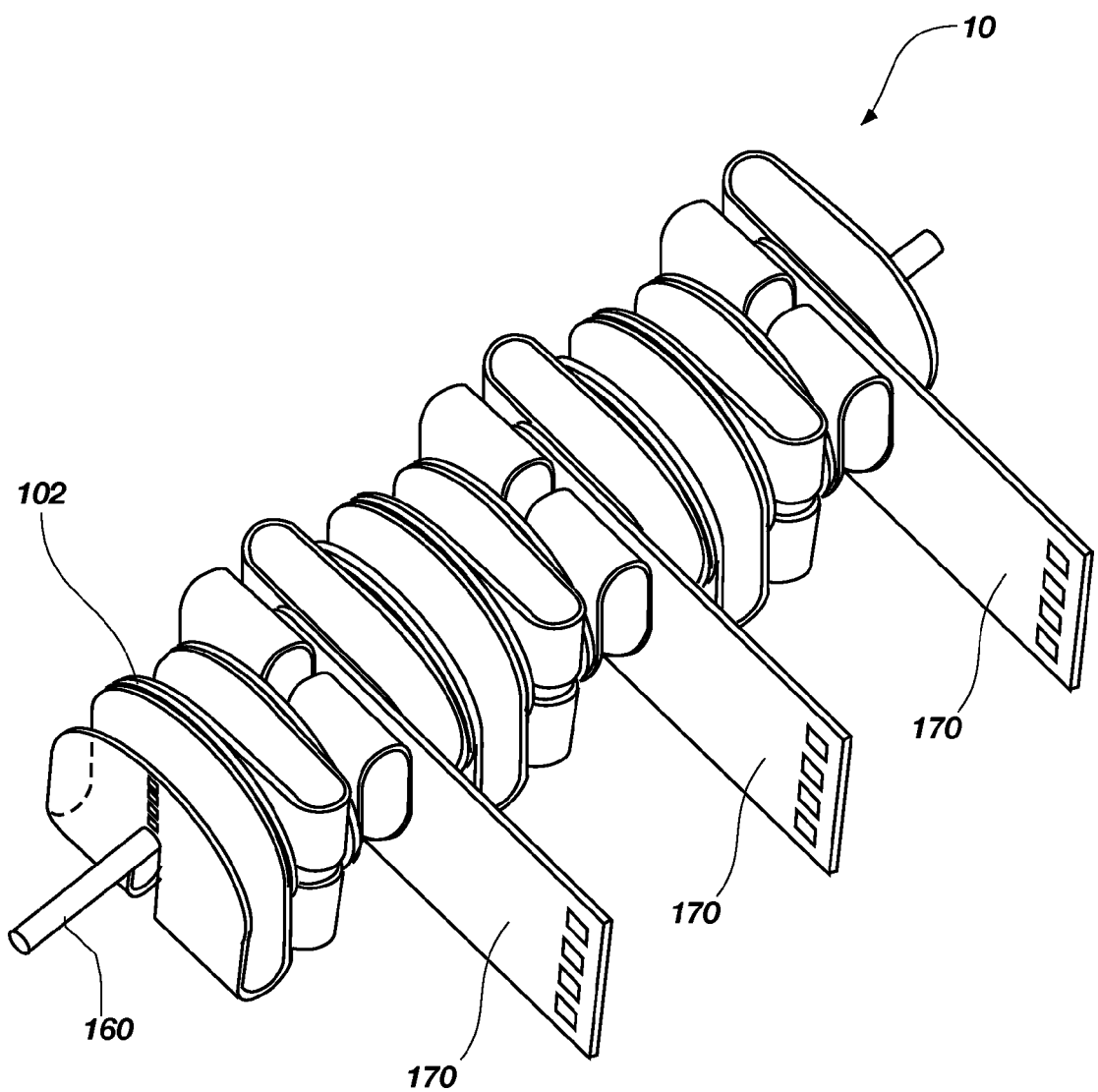
FIG. 6 illustrates the complex structure of FIG. 5 having a plurality of electrical taps in place to confirm the operation of any on-board systems existing on any of the stations.

With reference to FIG. 6, illustrated is a formed three-dimensional complex structure 10 with a plurality of electrical taps 170 situated about the central spine 160 and disposed between various stations on the complex structure 10. The electrical taps 170 may be used to confirm proper operation of any on-board systems existing on the various stations, and may then be broken off upon confirmation.

Figure 7:
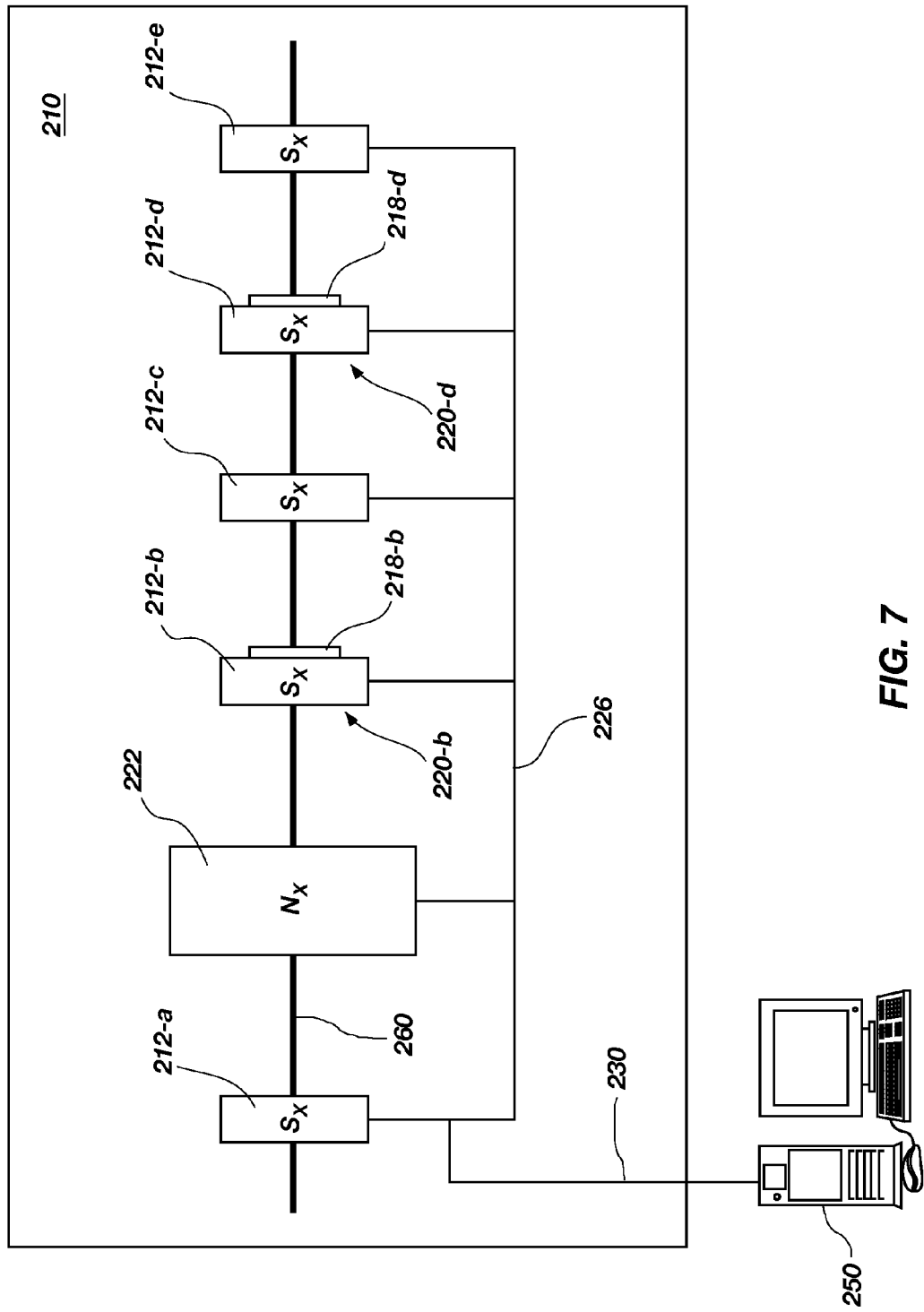
FIG. 7 illustrates a block diagram of a segment of a complex structure, according to one exemplary embodiment, wherein the complex structure comprises a plurality of stations and a node, all electrically interconnected, all addressed, and multiplexed together, with the complex structure being operably coupled to a computer.

FIG. 7 illustrates a graphical rendition of a three-dimensional complex structure formed from a two-dimensional layout, according to one exemplary embodiment of the present invention. Specifically, FIG. 7 illustrates the various interconnections between the several stations. As shown, the complex structure 210 comprises a plurality of stations, namely stations 212-a, 212-b, 212-c, 212-d, and 212-e. Each of these stations 212 are electrically interconnected to one another, and any nodes existing in the complex structure, such as node 222, via the electrical connection 226. As such, any one station 212 may communicate with any other station or any other node in the complex structure. Any on-board systems, shown in FIG. 7 as on-board systems 218-b and 218-d, are electrically connected to the station supporting it, in this case station 212-b and 212-d, respectively, thus allowing any station and associated on-board system to also communicate with any other station and/or on-board system, where appropriate. As indicated above, any station having an on-board system may be considered a performance station of some sort, thus FIG. 7 illustrates performance stations 220-b and 220-d. The electrical connection 226 shown is carried along the flexible interconnects (not shown) described above. This type of interconnection provides significant advantages over prior related interconnections as will be recognized by those skilled in the art.

In addition, each of these stations, and any nodes, may comprise an identifier or address $S_x$ (or $N_x$ in the case of a node), thus providing the complex 210 structure with a network of stations 212 and nodes 222.

The complex structure is further capable of being multiplexed together. Indeed, the flexible interconnects provide the ability to significantly reduce the number of electrical wires running between the various stations and a computer or other input source. In the embodiment shown, the complex structure 210 is electrically connected to computer 250 via connection 230.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

More specifically, while illustrative exemplary embodiments of the invention have been described herein, the present invention is not limited to these embodiments, but includes any and all embodiments having modifications, omissions, combinations (e.g., of aspects across various embodiments), adaptations and/or alterations as would be appreciated by those in the art based on the foregoing detailed description. The limitations in the claims are to be interpreted broadly based on the language employed in the claims and not limited to examples described in the foregoing detailed description or during the prosecution of the application, which examples are to be construed as non-exclusive. For example, in the present disclosure, the term "preferably" is non-exclusive where it is intended to mean "preferably, but not limited to." Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given above.

What is claimed and desired to be secured by Letters Patent is:

1. A two-dimensional layout for use in forming an elongate structure, said two-dimensional layout comprising:
   a support plate having a pre-determined, patterned recess formed in a surface thereof;
   a first series of individual flexible interconnects disposed in the patterned recess of the support plate, said first series of flexible interconnects having a pre-determined configuration based on the patterned recess;

at least one rigid member adhered to each of said first series of flexible interconnects; and a second series of individual flexible interconnects disposed in the patterned recess of the support plate and adhered to said rigid members, wherein an arrangement of a plurality of stations are formed, and wherein each of said second series of flexible interconnects is adhered to two rigid members of adjacent flexible interconnects of said first series.

2. The two-dimensional layout of claim 1, wherein said rigid member is adhered to said first and second series of individual flexible interconnects with a cured adhesive.

3. The two-dimensional layout of claim 1, further comprising an on-board system supported on at least one of said rigid members, wherein said on-board system and said station in support of said on-board system function as a performance station.

4. The two-dimensional layout of claim 3, wherein said performance station is selected from the group consisting of an intelligent performance station, an electrical performance station, a mechanical performance station, an actuation performance station, an information gathering performance station, a valving performance station, a pumping performance station, and an electro-mechanical performance station.

5. The two-dimensional layout of claim 3, wherein at least one of said first and second series of flexible interconnects comprises an electrical component that is electrically connected with said on-board system.

6. The two-dimensional layout of claim 1, further comprising a node disposed between adjacent stations.

7. The two-dimensional layout of claim 1, wherein said first and second series of flexible interconnects comprises a material selected from the group consisting of plastic, polymer, shape memory alloy and metalized polyimide film.

8. The two-dimensional layout of claim 1, wherein said first and second series of flexible interconnects and said at least one rigid member each comprise an aperture formed therein.

9. The two-dimensional layout of claim 1, wherein said second series of flexible interconnects are aligned parallel to one another and perpendicular to said first series of flexible interconnects.

10. The two-dimensional layout of claim 1, wherein said at least one rigid member is comprised of metal.

11. The two-dimensional layout of claim 1, wherein said rigid member is comprised of silicone, said rigid member functioning as a computer chip to facilitate one or more intelligent functions.

\* \* \* \* \*